(12) United States Patent  
Kotwica et al.

(10) Patent No.: US 6,479,719 B1  
(45) Date of Patent: Nov. 12, 2002

(54) METHOD AND REACTOR FOR MAKING NORBORNENE

(75) Inventors: Roland Kotwica, Pontpoint; André Marbach, Verneuil en Halatte, both of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/555,642

(22) PCT Filed: Nov. 23, 1998

(86) PCT No.: PCT/FR98/02494

§ 371 (c)(1), (2), (4) Date: Aug. 2, 2000

(87) PCT Pub. No.: WO99/28278

PCT Pub. Date: Jun. 10, 1999

(30) Foreign Application Priority Data

Dec. 2, 1997 (FR) .............................. 97 15160

(51) Int. Cl.$^7$ .............................. C07C 13/28; B01J 8/00; B01J 10/00
(52) U.S. Cl. ................. 585/360; 585/318; 585/354; 422/187; 422/188; 422/189
(58) Field of Search ................. 585/318, 354, 585/360; 422/187–189

(56) References Cited

U.S. PATENT DOCUMENTS 3,007,977 A    11/1961   Hill et al. ................. 585/318

4,022,591 A *  5/1977   Staudinger ................. 48/76

FOREIGN PATENT DOCUMENTS

| FR | 1 135 934 |   | 5/1957  |
|----|-----------|---|---------|
| GB |   855003  | * | 11/1960 |

OTHER PUBLICATIONS

"Ullmann's Encyclopedia of Industrial Chemistry, 5th edition, vol. B4" 1992, VCH VERLAG, Weinheim.

* cited by examiner

*Primary Examiner*—Thuan D. Dang  
(74) *Attorney, Agent, or Firm*—Millen, White, Zelano & Branigan, P.C.

(57) ABSTRACT

This process for the manufacture of norbornene from dicyclopentadiene (DCPD) and ethylene is characterized in that the DCPD is subjected to partial monomerization to CPD by preheating:

at a temperature of 140° C. to 240° C.; and under a pressure of 20 to 300 bar abs., before reacting it with the ethylene;

with an ethylene/DCPD molar ratio of 1 to 20;

at a temperature of 200° C. to 320° C.;

under a pressure of 20 to 300 bar abs.; and with a residence time of 1 to 10 minutes, under stable reaction conditions between the DCPD, the CPD and the ethylene.

19 Claims, 2 Drawing Sheets

METHOD AND REACTOR FOR MAKING NORBORNENE

FIELD OF THE INVENTION

The present invention relates to a process and to a reactor for the manufacture of norbornene (1,2,2-bicyclo[2.2.1]hept-2-ene) from dicyclopentadiene (DCPD) and ethylene.

BACKGROUND OF THE INVENTION

The synthesis of norbornene was described for the first time in 1941 by L. M. Joshel and L. W. Butz (J. Am. Chem. Soc., 63, 3350).

U.S. Pat. No. 2,340,908 discloses the reaction of DCPD and ethylene at a temperature of approximately 200° C. under a pressure of 50 to approximately 100 bar.

U.S. Pat. No. 3,007,977 discloses the synthesis of norbornene from a mixture of cyclopentadiene (CPD) and DCPD, the use of the mixture being regarded as favouring the control of the reaction conditions.

U.S. Pat. No. 3,763,253 discloses a highly selective process for the manufacture of norbornenes which consists of:
(1) introducing a mixture of a lower olefin and of DCPD having a temperature of greater than approximately 190° C., in particular of approximately 200–325° C., into a reactor with a substantial excess of olefin, for example at an olefin/DCPD molar ratio of 1:0.5 to 40:1,
(2) maintaining the conditions of temperature, of pressure and of residence time in the reactor so that the reactants and the products remain in the vapour phase and so that the formation of the norbornenes is favoured, in particular at a temperature of 200–325° C., a pressure of 6.8 to 136 Pa (100 to 2000 psi) and a residence time of 0.5 to 20 minutes, and
(3) recovering the norbornenes.

Patents DD-140,874 and DE-203,313 disclose a continuous process for the manufacture of norbornene by reaction of DCPD and/or CPD and ethylene under reaction conditions under which not only the reactants but also the desired norbornene are obtained in the gas phase, according to which process 1 mol of DCPD is mixed with 2–50 mol of ethylene and the reaction is carried out at 250–340° C. under a pressure of 2–20 MPa, excess ethylene being conveyed, before the reaction region, under the reaction pressure at a temperature of less than 190° C., through the liquid DCPD and then reacting to give the norbornene in the reaction region, the norbornene being withdrawn in the gaseous form at the top of the reaction region; according to DD-140,874, liquid compounds with high boiling points are withdrawn below the reaction region at temperatures of 150–220° C. in an amount of less than 3% by weight with respect to the DCPD introduced into the reaction system, their composition being regulated so as to comprise less than 1% by weight of norbornene; according to DE-203,313, liquid compounds with high boiling points are withdrawn from the region for mixing the DCPD with the ethylene, the liquid DCPD having a mean residence time in the mixing region of less than 60 minutes.

German Patent DD-144, 257 relates to a reactor for the synthesis of norbornene from DCPD and ethylene, the reaction space being divided by two concentrically positioned pipes into an annular space, in which cleavage of the DCPD predominantly takes place, and into an internal space, in which synthesis of the norbornene predominantly takes place.

German Patent DD-215, 078 relates to a process for the continuous manufacture of pure norbornene under reaction conditions according to which not only the reactants CPD and ethylene but also the norbornene are maintained in the gas phase; 1 mol of CPD is reacted with 1 to 25 mol of ethylene at 523–613° K. and under a pressure of 2–20 MPa; a DCPD concentrate, which comprises up to 20% of codimers of CPD with methylcyclopentadiene, piperylene, isoprene and butadiene, is mixed with the ethylene in a mixing region at 433–473° K. with a residence time of 10 to 30 minutes; the compounds with high boiling points formed in the mixing region are withdrawn at the lower end; the conversion to norbornene takes place in a reaction region following the mixing region and the reaction products are withdrawn at the top of the reaction region; the reaction products are separated in a two-stage distillation region which follows, so that methylnorbornene, methyltetrahydroindenes, DCPD and other by-products with high boiling points are withdrawn at the bottom of the first distillation stage and the light substances, such as CPD and small amounts of isoprene, of piperylene and of butadiene, are withdrawn at the top of the second distillation stage and norbornene of high purity is withdrawn at the bottom of the second distillation stage.

Processes for the synthesis of norbornene from DCPD or CPD have been provided in the literature but, in reality, such a synthesis is very difficult to carry out industrially because, due to the low reactivity of ethylene, it requires severe operating conditions. These operating conditions are very close to the conditions for the explosive thermal decomposition of (D)CPD. This is the reason why several industrial plants intended for the synthesis of norbornene have had to cease operations as a result of explosions.

The aim of the present invention is therefore to provide means which make it possible to carry out the industrial synthesis of norbornene under satisfactory safety conditions.

The difficulties of this synthesis will be set out in more detail in what follows.

Pure DCPD is solid at ambient temperature (M.p.= 305.15° Ki). DCPD is a dimer in equilibrium with its monomer, CPD, via a Diels-Alder reaction. The proportions of the two opposing products depends on the temperature and pressure conditions. The monomerization reaction is endothermic.

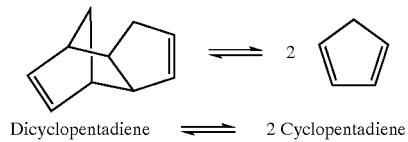

Dicyclopentadiene ⇌ 2 Cyclopentadiene

The reaction for the synthesis of norbornene is a Diels-Alder reaction between CPD (the diene) and ethylene (the dienophile).

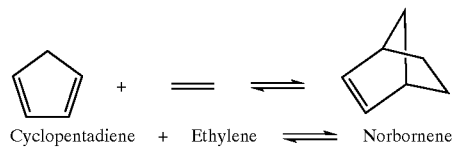

Cyclopentadiene + Ethylene ⇌ Norbornene

This reaction is an equilibrium reaction and theoretically results in a mixture of norbornene (Nor), CPD and DCPD being obtained.

The chemical factors which favourably influence the Diels-Alder reactions are:

a cyclic diene with a high ring strain, which is certainly the case with CPD;

a dienophile activated by an electron-withdrawing group, which is not the case with ethylene.

The reaction conditions have to be adjusted in order to compensate for this lack of reactivity of ethylene. The increase in pressure is a favourable thermodynamic and kinetic factor. The increase in temperature is a favourable kinetic factor but an unfavourable thermodynamic factor. The increase in the ethylene/CPD ratio is a favourable thermodynamic and kinetic factor.

The instability of the products introduces an additional constraint: safety. This is because it is recognized that the synthesis of norbornene is a risky reaction. The low reactivity of ethylene makes it necessary to operate under conditions which are close to the conditions for the explosive thermaldecomposition of the products.

The reaction between ethylene and CPD is strongly exothermic: $\Delta H°_{298}=-22$ kcal/mol ideal gas.

CPD is, in comparison with ethylene, the more sensitive product with regard to these explosive reactions. In 1991, a Union Carbide team (M. Ahmed and M. Lavin, Plant/Operation Progress, 1991, Vol., No. 3, pages 143–154) showed by DSC (differential scanning calorimetry) tests that CPD, heated under pressure, can successively give exothermic reactions at temperatures of:

250° C., formation of DCPD oligomers ($\Delta H=-66$ kcal/mol);

340° C., conversion of the oligomers to polymers ($\Delta H=-80$ kcal/mol);

440° C., decomposition of the polymers, resulting in the production of large amounts of gas ($\Delta H=-90$ kcal/mol).

The above recited temperatures are variable according to the source of the DCPD, without it having been possible to find an explanation for these variations, which can reach 30° C. ARC (accelerating rate calorimetry) tests were carried out and made it possible to record the pressure and temperature variations. In these tests, the final decomposition reaction stated at temperatures of 350° C. and resulted in increases in pressure of 5 bar (300° C.) to 210 bar (460° C.).

The reaction conditions are such that other condensation reactions come into play. Thus it is that dimethanooctahydronaphthalene (DMON) is formed.

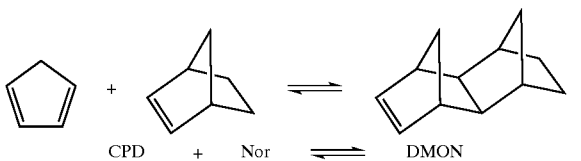

Likewise, the formation of tricyclopentadiene (TCPD) is observed.

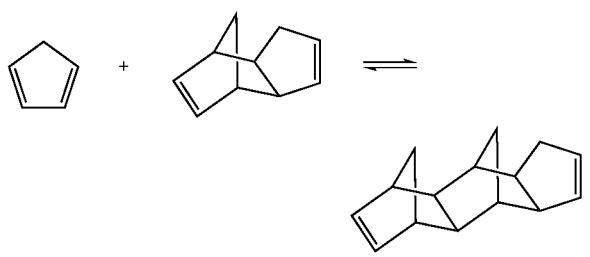

These reactions can continue and thus result in the formation of heavy products.

SUMMARY OF THE INVENTION

It has now been discovered that stable reaction conditions which make it possible to carry out the synthesis in question on an industrial scale can be obtained if two conditions are combined:

the partial monomerization of the DCPD; and the production of a fully controlled mixture between the (D)CPD and the ethylene.

Thus, according to the present invention, the synthesis of norbornene is carried out by two successively endothermic (monomerization of the DCPD to CPD) and then exothermic reactions. Surprisingly, and only experience allowed this result to be achieved, it is necessary to have partially monomerized the dicyclopentadiene to cyclopentadiene in order to obtain stable operation of the reaction. Theoretically, the endothermic reaction should be used as much as possible to control the overall exothermicity. The partial monomerization of the DCPD to CPD under pressure makes it possible to obtain a reactant which gives direct initiation of the reaction.

The partial monomerization of the dicyclopentadiene to cyclopentadiene is carried out in an exchanger. It is shown by thermodynamics that, under the pressure (150 bar) and temperature (175° C.) conditions, the equilibrium is shifted towards the formation of cyclopentadiene. The temperature was chosen so as to limit fouling of the exchanger and other side reactions. Experience has furthermore shown that, in contrast to intuition, preheating of the dicyclopentadiene is an important point in the intrinsic safety of the plant. The rise in temperature of the DCPD is separated from the reaction region (longer residence time and higher temperature), which limits the risks of drifting towards decomposition reactions.

A subject-matter of the present invention is a process for the manufacture of norbornene from dicyclopentadiene (DCPD) and ethylene, characterized in that the DCPD is subjected to partial monomerization to CPD by preheating:

at a temperature of 140° C. to 240° C.; and under a pressure of 20 to 300 bar abs., before reacting it with the ethylene with an ethylene/DCPD molar ratio of 1 to 20, in particular of 2 to 10;

at a temperature of 200° C. to 320° C.;

under a pressure of 20 to 300 bar abs.; and with a residence time of 1 to 10 minutes, in particular of 1.5 to 3 minutes, under stable reaction conditions between the DCPD, the CPD and the ethylene.

The preliminary preheating of the DCPD is conveniently carried out in an exchanger and the reaction proper in a reactor comprising a device which makes possible homogeneous and rapid mixing of the reactants, in order to avoid local overheating, thus eliminating the risks of explosion. The device for the homogeneous and rapid mixing of the reactants is advantageously a device which makes use of the injection of supercritical ethylene in order to disperse the DCPD, preventing the liquid DCPD from ever becoming motionless under the conditions of the reaction. To this end, the reactants arrive in the reactor via the bottom, the DCPD or DCPD-CPD being injected via a first pipe which is positioned axially and which extends over a portion of the height of the reactor and the ethylene being injected via a second coaxial pipe which surrounds the first into the annular region between the two pipes.

In accordance with other characteristics of the process of the present invention:

the ethylene is placed under the temperature and pressure conditions of the reaction region before being introduced into the latter;

the crude norbornene exiting from the reaction region is cooled and subjected to at least one degassing which makes it possible to remove ethylene at the top and to obtain purified norbornene at the bottom; and the ethylene resulting from the degassing is washed countercurrent wise by the incoming DCPD flow, before being recycled in the incoming ethylene flow.

Another subject-matter of the present invention is a reactor for the manufacture of norbornene from dicyclopentadiene and ethylene, characterized in that it comprises a device for the injection of the reactants arranged in order for the ethylene in the supercritical state to disperse the liquid DCPD or the liquid DCPD-CPD mixture substantially completely under the conditions of the reaction.

In particular, the abovementioned injection device comprises two coaxial pipes for delivery of the reactants via the bottom of the reactor, the said pipes extending axially over a portion of the height of the said reactor, the DCPD or the DCPD-CPD arriving via the central pipe and the ethylene via the annular space between the two pipes, the top part of the system constituting a region of intense mixing of the reactants and the bottom part a region for turbulent flow of the crude norbornene produced, which is discharged via the bottom of the reactor.

The characteristics of the present invention will now be described in more detail with reference to the appended drawing, in which.

Figure 1:
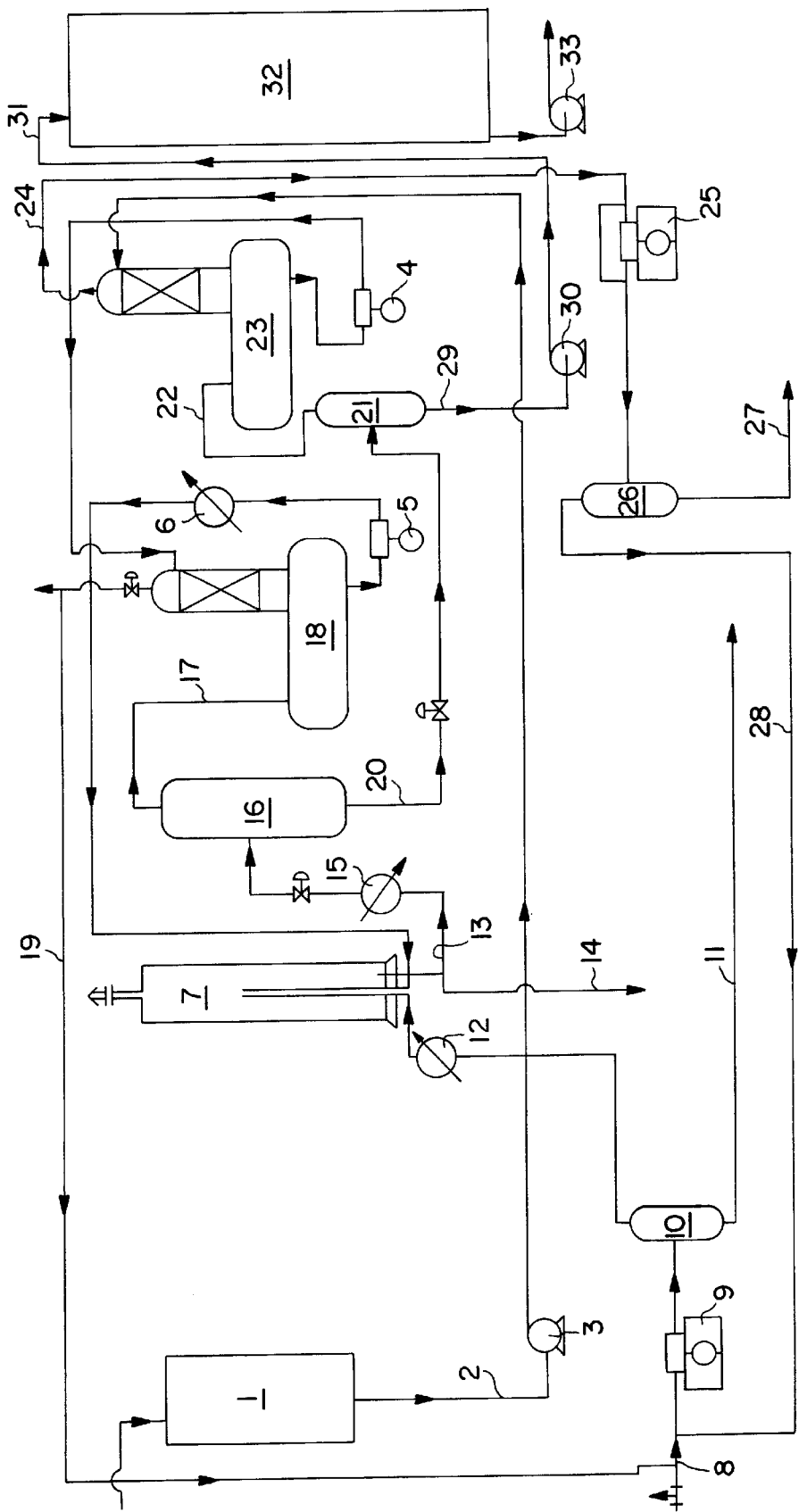
FIG. 1 is a general diagram of the plant.

If reference is made to FIG. 1, it can be seen that the DCPD, stored in a vessel 1, arrives via the line 2 and is pressurized by the pumps 3, 4 and 5. As will be described hereinbelow, it is used to wash the ethylene to be recycled which is given off during the degassing of the norbornene obtained.

Before entering the reactor 7, the DCPD is subjected to preheating in the exchanger 6 under the conditions which make it possible to partially monomerize it to CPD.

In parallel, the ethylene arriving via the pipe 8 is pressurized in the compressor 9, bled in the tank 10 via the bleed pipe 11 and raised in temperature in the exchanger 12. It enters the reactor 7 at the reaction pressure.

At the outlet of the reactor 7, the norbornene/ethylene mixture 13, bled at 14, is cooled in the exchanger 15. The mixture is subsequently reduced in pressure and then degassed in a degassing vessel 16. The ethylene resulting from this degassing, exiting via the line 17, is washed with the DCPD in the washing plant 18 and is recycled in the synthesis via the line 19.

The mixture exiting at the bottom 20 of the tank 16 is reduced in pressure and is sent to a degassing vessel 21 in which it is again degassed. The ethylene exiting at the top 22 of the vessel 21 is sent to a washing plant 23 in which it is washed with the DCPD. The ethylene exiting at the top 24 of the plant 23, pressurized by a compressor 25, is sent to a tank 26, from where it is bled at 27, and then it is sent via the line 28 into the line 8 upstream of the compressor 9.

The crude norbornene exiting at the bottom 29 of the tank 21 is pressurized by the pump 30 and is then conveyed via the line 31 into a storage tank 32, from where it can be pumped (at 33) in order to be sent to the distillation.

Figure 2:
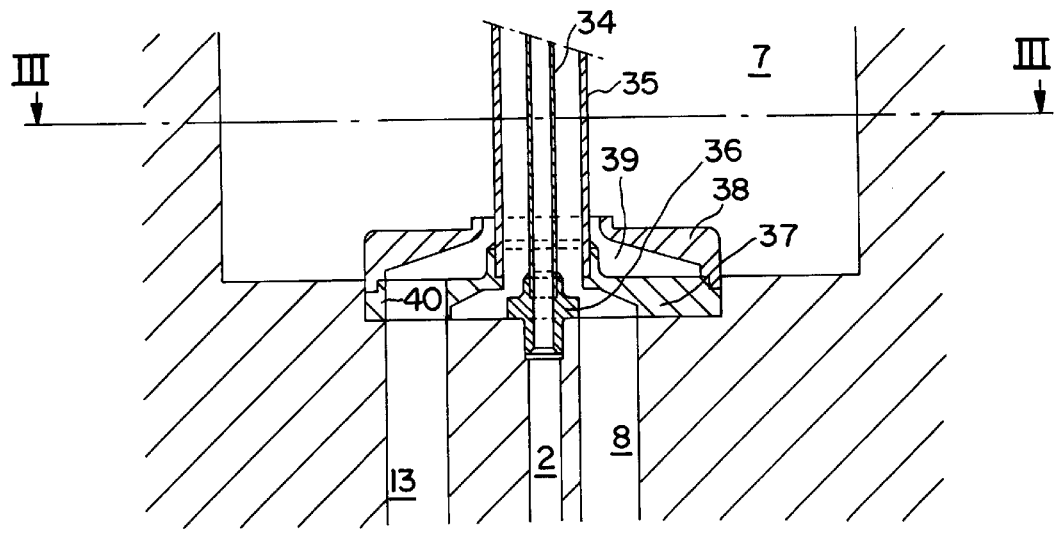
FIG. 2 is a partial view in longitudinal axial cross section of the synthesis reactor.
Figure 3:
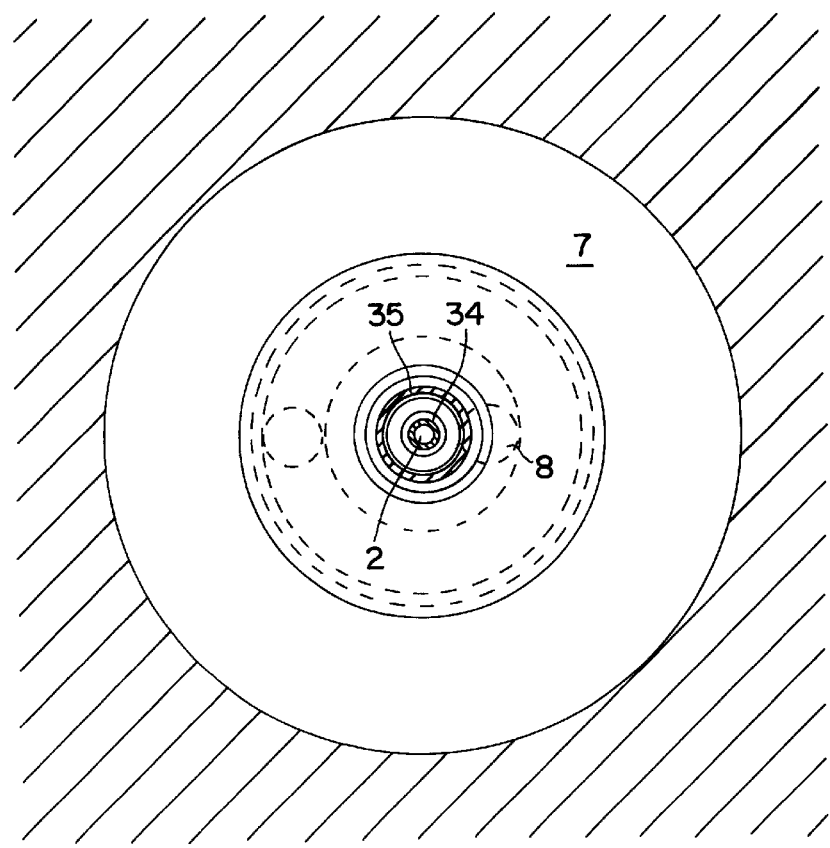
FIG. 3 is a view in transverse cross section along III—III of FIG. 2.

If reference is now made to FIGS. 2 and 3, it can be seen that the lower part of the reactor 7, showing the inlet for the reactants, has been represented.

The reactor 7 is a cylindrical reactor with a vertical axis. The reactants arrive via the bottom and enter a system of two coaxial pipes 34, 35 which extend along the longitudinal axis of the reactor 7 over a little more than half the height of the latter.

The internal pipe 34 is received in a seating 36 fixed against the bottom of the reactor 7 and comprising a central orifice in communication with the inlet line 2 for the DCPD.

The external pipe 35 is received in the central part of an annular seating 37 fixed against the bottom of the reactor 7 and in communication with the ethylene inlet line 8, which emerges laterally in the central opening of the seating 37.

A third annular seating 38, comprising a central opening through which passes the system of pipes 34, 35, is fixed via its periphery to the periphery of the seating 37 while being separated from the latter by an annular space 39. The crude norbornene is discharged via the space left free between the internal edge of the seating 38 and the pipe 35 into the annular space 39 and exits via an opening 40 made in the seating 37 which is on the other side from the inlet for the ethylene and is in communication with the outlet pipe 13.

The ethylene arrives in the reactor 7 in the supercritical state via the space between the pipes 34 and 35 and the DCPD arrives in the pipe 34 in the liquid state and while being partially monomerized. The speed of the ethylene increases by virtue of the shape of the nozzle.

Good mixing of the reactants is obtained by the acceleration of ethylene at the narrowing, which results in the dispersion of the DCPD. This dispersion is improved by the monomerization of the residual DCPD, which generates supercritical CPD. The DCPD in fact arrives in the form of a jet which does not strike the top of the reactor.

A region of intense mixing is found in the top part of the reactor (above the free end of the twin-pipe system), this region being followed (lower part of the reactor) by a region for turbulent flow (Re=88,000).

The plant which has just been described with reference to the appended drawing has been used to carry out syntheses of norbornene under different operating conditions (Examples 1 to 3). These conditions and the production of the crude norbornene are summarized in Table 1.

TABLE 1

| Operating conditions Example | Washing device 23 | | | Degassing vessel 21 | Washing device 18 | | Degassing vessel 16 | | Flow rate for the crude synthetic product (kg/h) |
|---|---|---|---|---|---|---|---|---|---|
| | DCPD feed flow rate (kg/h) | Temperature (° C.) | Pressure (bar eff.) | Temperature (° C.) | Temperature (° C.) | Pressure (bar eff.) | Temperature (° C.) | Pressure (bar eff.) | |
| 1 | 270 | 57 | 0.58 | 34 | 48 | 10.14 | 40 | | 458 |
| 2 | 554 | 54 | 0.62 | 38 | 54 | 10.76 | 43 | 7.6 | 764 |
| 3 | 602 | 50 | 0.6 | 37 | 56 | 11.1 | 49 | 7.8 | 821 |

| Operating conditions Example | Ethylene feed | | | | | | | | | Preheater 12 outlet temperature (° C.) |
|---|---|---|---|---|---|---|---|---|---|---|
| | Fresh ethylene flow rate (kg/h) | Compressor flow flow rate (kg/h) | Compressor 9 suction flow rate (kg/h) | Compressor 9 suction temperature (° C.) | Compressor 9 lift temperature (° C.) | Compressor 9 suction pressure (bar eff.) | Compressor 9 lift pressure (bar eff.) | Compressor 25 suction pressure (bar eff.) | Compressor 25 lift pressure (bar eff.) | |
| 1 | 188 | 27 | 962 | 30.9 | 60 | 8.1 | 140 | 0.58 | 8.5 | 240 |
| 2 | 210 | 32 | 1151 | 36 | 59 | 9.9 | 138 | 0.62 | 10 | 229 |
| 3 | 219 | 34 | 1173 | 28 | 54 | 9.6 | 139 | 0.6 | 10 | 230 |

| Operating conditions Example | DCPD feed | | | Reactor 7 | | Production of crude nornornene (t/day) |
|---|---|---|---|---|---|---|
| | Preheater 6 outlet temperature (° C.) | Preheater 6 outlet flow rate (kg/h) | Content of CPD + DCPD (%) | Ethylene/DCPD molar ratio* | Temperature (° C.) | |
| 1 | 172 | 490 | 88.808 | 5.2 | 309 | 11 |
| 2 | 176 | 650 | 88.234 | 4.7 | 312 | 18.3 |
| 3 | 175 | 720 | 87.165 | 4.4 | 311 | 19.7 |

*Calculated by regarding the ethylene as pure as by taking into account the content of CPD and DCPD in the feed.

What is claimed is:

1. In a process for the manufacture of norbornene from dicyclopentadiene (DCPD) and ethylene, the improvement comprising subjecting the DCPD to partial monomerization to CPD by preliminary preheating:
   at a temperature of 140° C. to 240° C.; and
   under a pressure of 20 to 300 bar abs., before reacting the DCPD with the ethylene, the reaction with ethylene being conducted thereafter;
   with an ethylene/DCPD molar ratio of 1 to 20;
   at a temperature of 200° C. to 320° C.;
   under a pressure of 20 to 300 bar abs.; and
   with a residence time of 1 to 10 minutes, under stable reaction conditions between the DCPD, the CPD and the ethylene.

2. A process according to claim 1, wherein the reaction is carried out with an ethylene/DCPD molar ratio of 2 to 10.

3. A process according to claim 1, wherein the reaction with the ethylene is carried out with a residence time of 1.5 to 3 minutes.

4. A process according to claim 1, wherein the preliminary preheating of the DCPD is carried out in an exchanger.

5. A process according to claim 1, wherein the reaction is carried out in a zone providing homogenous and rapid mixing of the reactants, wherein ethylene is injected in the supercritical state in order to disperse the liquid DCPD under the conditions of the reaction.

6. A process according to claim 1, wherein the ethylene is provided under the temperature and pressure conditions of the reaction before being introduced into the reactor.

7. A process according to claim 1, wherein crude norbornene exiting from the reaction region is cooled and subjected to at least one degassing step to remove ethylene at the top and to obtain purified norbornene at the bottom.

8. A process according to claim 7, wherein the ethylene resulting from the degassing is washed countercurrently to incoming DCPD flow, before being recycled in the incoming ethylene flow.

9. A reactor system for the manufacture of norbornene from dicyclopentadiene and ethylene reactants, comprising:
   means for providing a source of supercritical ethylene,
   a source of liquid DCPD or liquid DCPD-CPD,
   a device for the injection of the reactants arranged in order for the ethylene in the supercritical state to disperse the liquid DCPD or the liquid DCPD-CPD mixture substantially completely under reaction conditions,
   said injection device comprising at least two coaxial pipes for delivery of the reactants via the bottom of the reactor,
   said pipes extending axially over a portion of the height of said reactor, means for communicating the source of the DCPD or the DCPD-CPD with the central pipe and means for communicating the source of the supercritical ethylene with the annular space between the two pipes,
   a top zone of the reactor system comprising means for providing intense mixing of the reactants and a bottom zone of the reactor system comprising means for providing turbulent flow of the crude norbornene produced, which is discharged via a bottom of the reactor.

10. A process according to claim 1, wherein the DCPD is preheated to 172–176° C.

11. A process according to claim 1, wherein the ethylene/DCPD molar ratio in the reactor is 4.4:1 to 5.2:1.

12. A process according to claim 1, wherein the reactor temperature is 309–311° C.

13. A process according to claim 1, where the reactants are mixed in a turbulent flow having a Reynolds number of at least 88,000.

14. A process according to claim 1, further comprising the steps of:
   raising the pressure of the ethylene to the reaction pressure within the reactor, and
   raising the temperature of the ethylene such that the ethylene is a supercritical fluid at reaction pressure.

15. A process according to claim 14, wherein the ethylene is raised to a pressure of 138–140 bar.

16. A process according to claim 14, wherein the ethylene is preheated to a temperature of 230–240° C.

17. A process for the manufacture of norbornene from dicyclopentadiene and ethylene reactants in a reactor system, wherein the reactants are the ethylene and one of liquid DCPD or liquid DCPD-CPD, comprising:
   a) arranging the reactants in order such that the ethylene will disperse the liquid DCPC or the liquid DCPC-CPD mixture substantially completely under reaction conditions, wherein the ethylene is in a supercritical state,
   b) injecting the reactants into the reactor with an injection device,
      wherein the injection device comprises at least two coaxial pipes for delivery of the reactants via the bottom of the reactor,
      and wherein the pipes extend axially over a bottom zone of the height of said reactor such that, the DCPD or the DCPD-CPD arrives in the reactor via the central pipe and the ethylene via an annular space between the two pipes,
   c) mixing the reactants in a top zone of the reactor system,
   d) collecting and discharging a flow of the crude norbornene produced, via a bottom zone of the reactor.

18. A process according to claim 17, further comprising the steps of:
   raising the pressure of the ethylene to the reaction pressure within the reactor, and
   raising the temperature of the ethylene such that the ethylene is a supercritical fluid at reaction pressure.

19. A reactor system according to claim 9, wherein said means for providing supercritical ethylene comprises:
   at least one compressor, and
   at least one an exchanger,
   wherein the at least one compressor is capable of raising the pressure of the ethylene to the reaction pressure within the reactor,
   and wherein the at least one exchanger is capable of raising the temperature of the ethylene such that the ethylene is a supercritical fluid at reaction pressure.

\* \* \* \* \*